US008415640B2

(12) United States Patent
Babinec et al.

(10) Patent No.: US 8,415,640 B2
(45) Date of Patent: Apr. 9, 2013

(54) DIAMOND NANOWIRES

(75) Inventors: Thomas M. Babinec, Watertown, MA (US); Birgit J. M. Hausmann, Watertown, MA (US); Mughees Khan, Belmont, MA (US); Yinan Zhang, Cambridge, MA (US); Philip R. Hemmer, College Station, TX (US); Marko Loncar, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/089,547

(22) Filed: Apr. 19, 2011

(65) Prior Publication Data

US 2011/0309265 A1  Dec. 22, 2011

Related U.S. Application Data

(60) Provisional application No. 61/325,543, filed on Apr. 19, 2010.

(51) Int. Cl.
   *G01N 21/64* (2006.01)
(52) U.S. Cl.
   USPC .................................................. 250/458.1
(58) Field of Classification Search ........... 250/459.1
   See application file for complete search history.

(56) References Cited

U.S. PATENT DOCUMENTS

2006/0284118 A1* 12/2006 Asmussen et al. ....... 250/492.21
2008/0268288 A1* 10/2008 Jin ................................ 428/800

OTHER PUBLICATIONS

Faklaris et al., "Photoluminescent ranodiamonds: Comparision of the photoluminescence saturation properties of the NV color center and a cyanine dye at the single emitter level, and study of the color center concentration under different preparation conditions," 2010, Diamond & Related Materials, vol. 19, pp. 988-995.*
Smirnov et al., "Aligned diamond nano-wires: Fabrication and characterisation for advanced applications in bio and electrochemistry," 2010, Diamond & Related Materials, vol. 19, pp. 186-189.*
Babinec et al., "A diamond nanowire single-photon source," Feb. 14, 2010, Nature Nanotechnology Letters, pp. 195-199.*
Hiscocks, et al., "Diamond Waveguides Fabricated by Reactive Ion Etching," Optics Express, vol. 16, No. 24, Nov. 24, 2008.

* cited by examiner

*Primary Examiner* — Kiho Kim
(74) *Attorney, Agent, or Firm* — Occhiuti Rohlicek & Tsao LLP

(57) ABSTRACT

In a general aspect, a system includes a plurality of diamond nanowires disposed on the surface of a diamond substrate, at least some of the nanowires including a color center. The system also includes a light source configured to illuminate at least one of the plurality of nanowires with excitation light at a wavelength corresponding to an excitation wavelength of the color center included in the illuminated nanowire; and an optical receiver configured to receive a fluorescence emitted from the color center included in the illuminated nanowire in response to the excitation light.

23 Claims, 13 Drawing Sheets

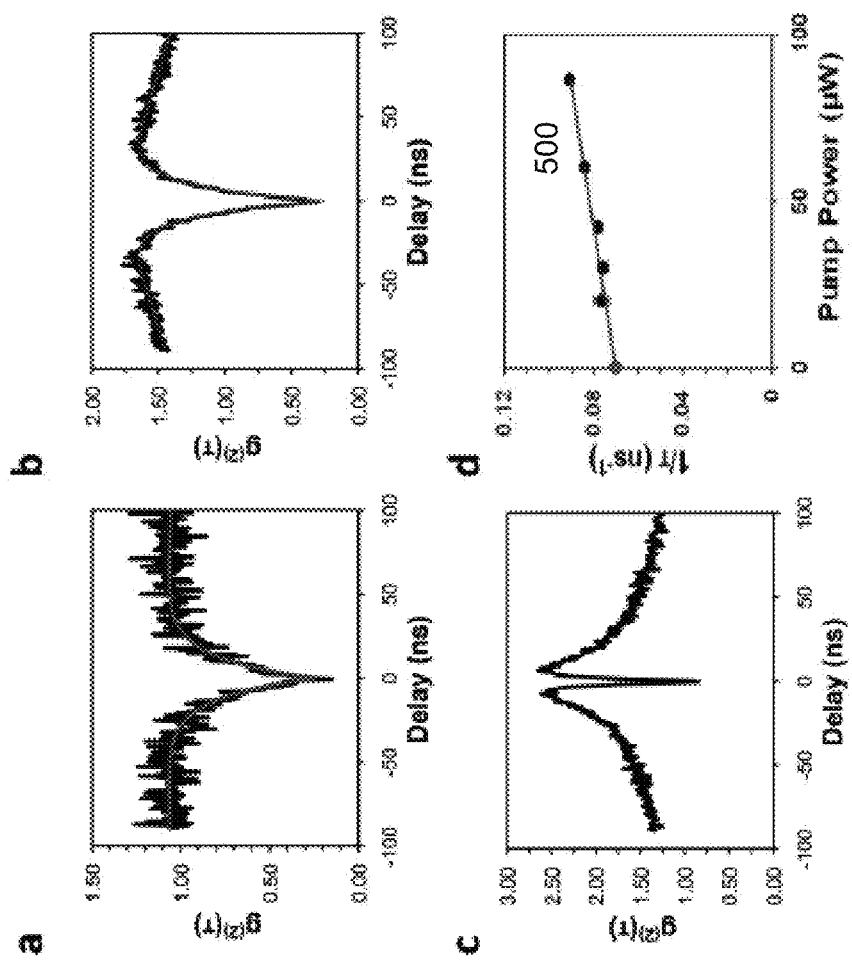
FIG. 5A-D

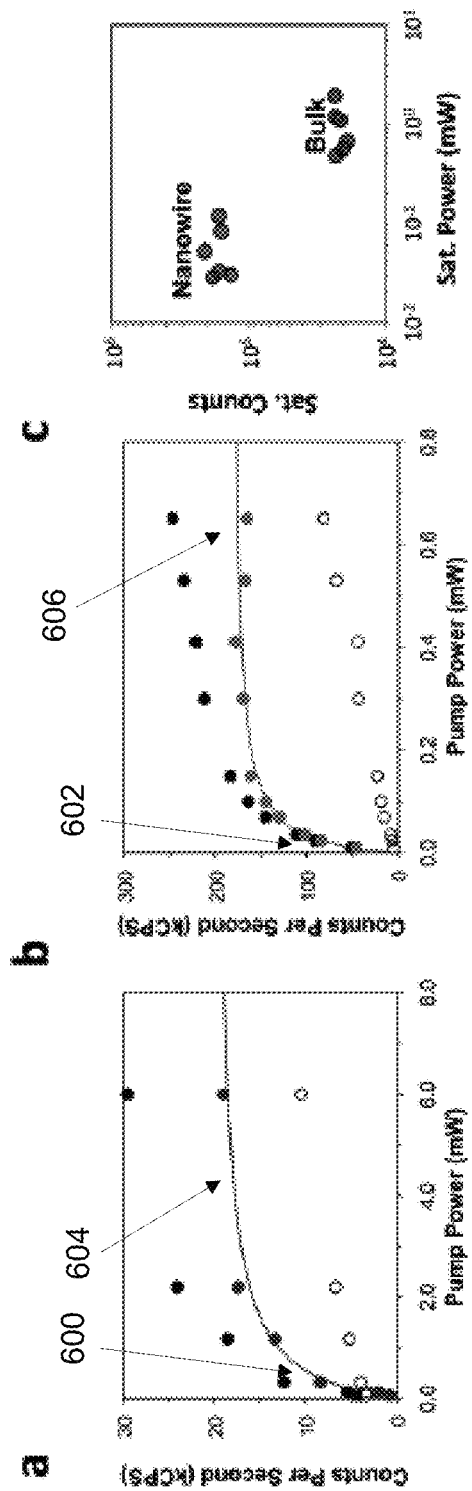
FIG. 6A-C

DIAMOND NANOWIRES

CROSS-REFERENCE TO RELATED APPLICATIONS

This application claims priority to U.S. Provisional Application Ser. No. 61/325,543, filed Apr. 19, 2010, and entitled "Diamond Nanowires," the contents of which are incorporated herein by reference.

STATEMENT REGARDING FEDERALLY SPONSORED RESEARCH OR DEVELOPMENT

This invention was made with Government support under National Science Foundation awards ECCS-0708905 and PHY-0646094 and DARPA awards C09-00511 and HR0011-09-1-0006. The Government has certain rights in the invention.

BACKGROUND

The development of a robust light source that emits one photon at a time will enable new technologies such as perfectly secure communication via quantum cryptography. Devices based on fluorescent dye molecules, quantum dots, and carbon nanotubes have been demonstrated, but in general these devices do not combine a high single photon flux with stable, room-temperature operation. Luminescent centers in diamond have recently emerged as a candidate for these applications.

Color centers based on Nitrogen, Silicon, Carbon, Nickel, and Chromium impurities have all been demonstrated to emit single photons at room temperature. The Nitrogen-vacancy (NV) center possesses additional electron and nuclear spin degrees of freedom with a long coherence time. NV centers can thus act as a quantum memory for long distance quantum communications, quantum computing, and nanoscale magnetometry. Light-matter interactions, and in particular in- and out-coupling of photons, can be engineered by embedding emitters such as a Nitrogen-vacancy (NV) center within nanophotonic structures. One approach to such coupling is to evanescently couple a separate optical cavity or a waveguide to a proximal NV center. Another approach is to realize optical structures directly in thin diamond films grown on foreign (low-index or sacrificial) substrates, such as polycrystalline diamond films. Devices such as planar photonic crystals or microdisk resonators may also be sculpted from a bulk diamond crystal.

SUMMARY

In a general aspect, a system includes a plurality of diamond nanowires disposed on the surface of a diamond substrate, at least some of the nanowires including a color center. The system also includes a light source configured to illuminate at least one of the plurality of nanowires with excitation light at a wavelength corresponding to an excitation wavelength of the color center included in the illuminated nanowire; and an optical receiver configured to receive a fluorescence emitted from the color center included in the illuminated nanowire in response to the excitation light.

Embodiments may include one or more of the following.

The optical receiver is at least one of an optical fiber and a detector.

Each nanowire has a diameter of about 200 nm and a length of about 2 μm. The length of the nanowires is in a direction perpendicular to the surface of the substrate.

A lifetime of the fluorescence emitted from the at least one color center is between about 10 ns and about 25 ns, or about 15 ns.

A first end of the illuminated nanowire is in contact with the surface of the substrate, and wherein the optical receiver is positioned to receive the emitted fluorescence from a distal end of the illuminated nanowire. The fluorescence is emitted from the at least one color center in a mode propagating perpendicularly away from the surface of the substrate.

The optical receiver is positioned to receive at least 10% of the emitted fluorescence, or about 40% of the emitted fluorescence.

The fluorescence emitted from the at least one color center includes at least 50,000 photons per second, or at least 100,000 photons per second.

The diamond substrate is crystalline. The surface of the diamond substrate is a {100} type surface or a {111} type surface.

The illuminated nanowire is configured to emit fluorescence at a temperature greater than about 300 K.

In another general aspect, a method includes providing a diamond substrate; and selectively removing a portion of the surface of the substrate to provide a plurality of diamond nanowires.

Embodiments may include one or more of the following.

The diamond substrate includes a plurality of color centers; and wherein selectively removing the portion of the surface of the substrate includes selectively removing a portion of the surface of the substrate in a region including at least one color center. The plurality of color centers in the diamond substrate are distributed substantially randomly.

The method further includes implanting at least one color center in at least some of the plurality of diamond nanowires.

The method further includes forming a microelectromechanical systems (MEMS) or nanoelectromechanical systems (NEMS) device including at least one of the plurality of diamond nanowires. The MEMS or NEMS device includes at least one of a mechanical resonator and an atomic force microscopy (AFM) probe.

The method further includes illuminating at least some of the plurality of nanowires with excitation light at a wavelength corresponding to an excitation wavelength of the nitrogen vacancy centers; and receiving a fluorescence emitted from at least one nitrogen vacancy center in response to the excitation.

Receiving the fluorescence includes detecting at least 10% of the emitted fluorescence, or about 40% of the emitted fluorescence. Receiving the fluorescence includes receiving the fluorescence into an optical fiber.

Selectively removing a portion of the surface of the substrate includes fabricating nanowires with diameter of about 200 nm and a length of about 2 μm.

Selectively removing a portion of the surface of the substrate includes: lithographically defining a pattern on the surface of the substrate corresponding to an arrangement of the nanowires; and etching the surface of the substrate according to the lithographically defined pattern.

Etching the surface of the substrate includes performing a reactive ion etch for about 10 minutes. Performing the reactive ion etch includes: applying an inductively coupled plasma (ICP) power of about 700 W for about two minutes; applying an ICP power of about 600 W for about three minutes; and applying an ICP power of about 1000 W for about five minutes. Performing the reactive ion etch includes performing the etch in an atmosphere of 30 sccm of oxygen gas and at a pressure of 10 mTorr. Performing the reactive ion etch includes performing the etch at a bias power of about 100 W.

Providing the diamond substrate includes providing a crystalline diamond substrate. Selectively removing a portion of the surface of the substrate includes fabricating the nanowires on a {100} type surface or a {111} type surface of the diamond substrate.

Among other advantages, the systems and methods described herein combine a high single photon flux with stable, room-temperature operation of a diamond nanowire photon source. For instance, a photon flux ten times greater than that available from a bulk diamond can be produced while using ten times less power. Diamond nanowires including any of a variety of color centers, including but not limited to nitrogen vacancy centers, may be fabricated, allowing the emission wavelength to be selected.

The diamond nanowire photon source herein is capable of emitting photons both at room temperature and at cryogenic temperatures (e.g., about 4 K). High photon flux is achievable in both temperature ranges. Diamond nanowire photon sources at cryogenic temperatures have applications, e.g., in the field of communications.

The top-down parallel fabrication techniques maintain important properties of the color centers in diamond nanowires and are compatible with criteria for the realization of scalable diamond-based quantum systems. Fabrication is straightforward and can be integrated with existing fabrication processes and infrastructure. Background fluorescence generated by processing diamond with nanofabrication methods is not prohibitively high.

Other features and advantages of the invention are apparent from the following description and from the claims.

BRIEF DESCRIPTION OF DRAWINGS

FIGS. 5A-5C are plots of the $g^{(2)}(\tau)$ autocorrelation function for excitation powers of 11 µW, 190 µW, and 1.6 mW, respectively.

FIG. 5D shows the decay rate of the $g^{(2)}(\tau)$ autocorrelation function spectrum for different excitation conditions.

FIGS. 6A and 6B are plots of the number of single photons per second collected from a single NV center in an ultra-pure bulk diamond crystal and in a diamond nanowire, respectively.

FIG. 6C is a plot showing the distribution of the single photon device properties for bulk diamond devices and diamond nanowire devices.

DETAILED DESCRIPTION

Figure 1A:
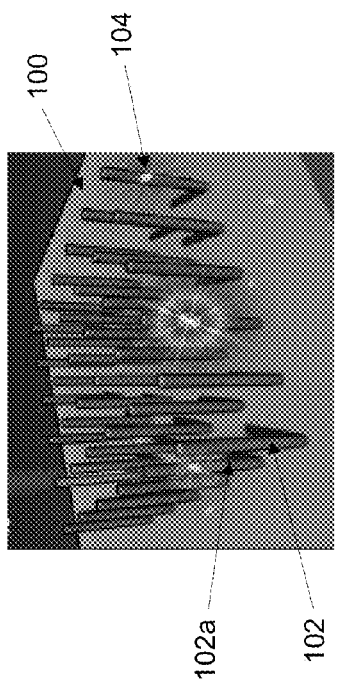
FIG. 1A is a schematic diagram of a diamond nanowire array.
Figure 1B:
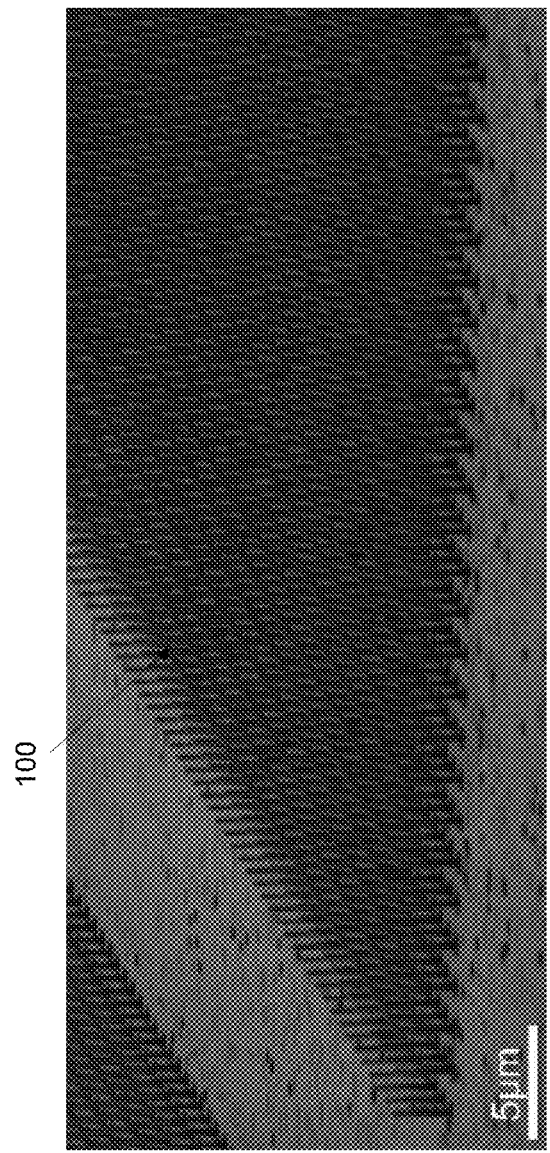
FIG. 1B is a scanning electron microscopy (SEM) image of a diamond nanowire array.

Referring to FIGS. 1A and 1B, a diamond nanowire array 100 includes vertically oriented diamond nanowires 102, with Nitrogen vacancy (NV) centers 104 randomly distributed among the nanowires 102. Upon excitation with light at the appropriate excitation wavelength of the NV centers, each nanowire that incorporates an NV center 104 (e.g., nanowire 102a) acts as an efficient single photon source. Specifically, and as discussed in greater detail below, an NV center in the nanowire acts as a high-flux source of single photons due to an antenna effect that modifies its radiation pattern. Diamond nanowire array 100 can be fabricated over a large area, e.g., hundreds of square microns.

Figure 2:
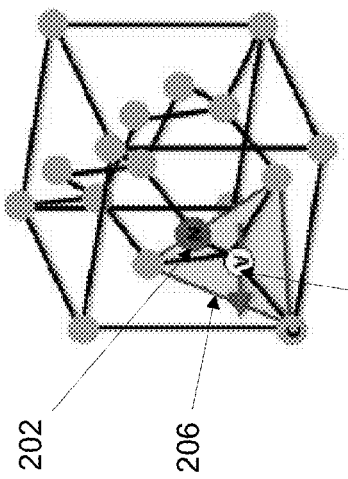
FIG. 2 is a schematic diagram of a diamond unit cell including a Nitrogen vacancy (NV) center.

Referring to FIG. 2, an NV center is a crystallographic defect formed of a substitutional Nitrogen atom 202 and an adjacent lattice vacancy 204 in the crystal lattice of diamond. NV centers are naturally created during the crystal growth process and are randomly distributed throughout bulk diamond. Because of a dipole transition that is polarized in the {111}-type crystal plane (shown as a shaded triangle 206), broadband single photon emission is possible from an NV center.

Optical Measurements of Diamond Nanowires

Figure 3A:
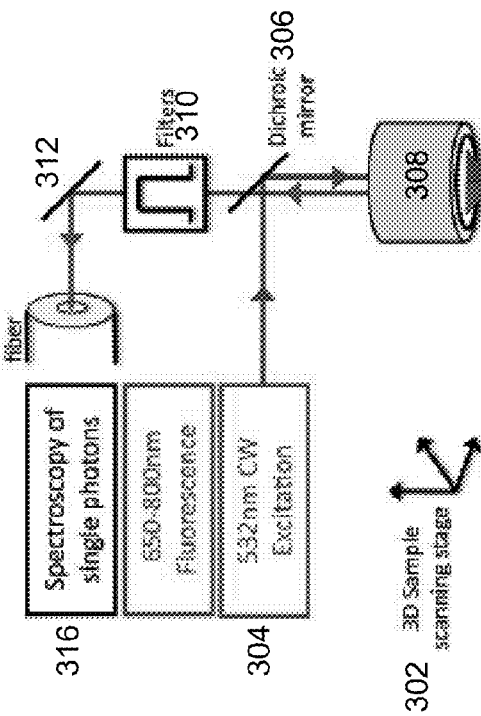
FIG. 3A is a block diagram of an optical system operating on a diamond nanowire array
Figure 3B:
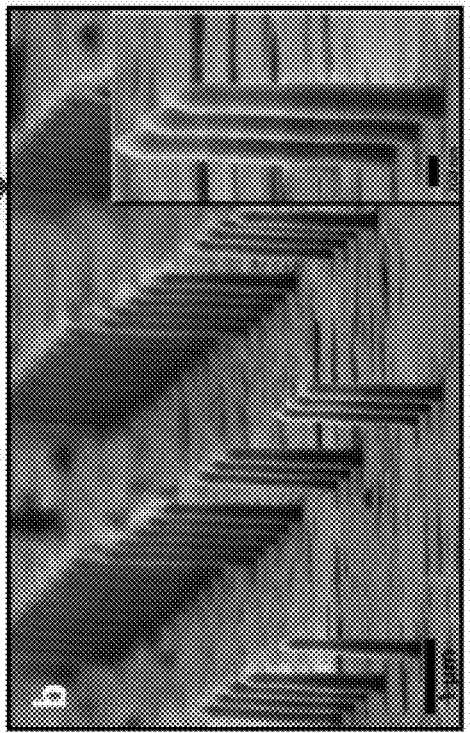
FIG. 3B is a scanning electron microscopy (SEM) image of a diamond nanowire array (main scale bar 1 µm; inset scale bar 200 nm).

Referring to FIGS. 3A and 3B, an optical system 300 provides excitation light at the excitation wavelength of the NV centers and collects the fluorescence emitted by the excited NV centers. Optics system 300 is located on a 3D sample scanning stage 302 which controls the relative motion of the optics system 300 relative to diamond nanowire array 100 and thus allows the optics system to address each individual diamond nanowire 102 individually.

In one embodiment, optical system 300 is a scanning confocal microscope that includes a light source 304, such as a 532 nm continuous wave (CW) laser. The light output from light source 304 is reflected toward nanowire array 100 by a dichroic mirror 306. An objective lens 308, such as an air objective lens (NA=0.95), is used to focus the green pump light from light source 304 onto one of the nanowires 102 in array 100.

In response to the excitation light, nanowires that incorporate an NV center 104 fluoresce (e.g., at 650-800 nm). The fluorescence of those nanowires is collected by objective lens 308, transmitted through dichroic mirror 306, filtered by a filter 310, and directed by a mirror 312 into a single mode fiber 314. Single mode fiber 314 acts as a confocal pinhole, rejecting unfocused light. The light collected by single mode fiber 314 arrives at a spectroscopy module 316 (e.g., a photodetector), where spectroscopic analysis of the light can be conducted. In general, at least 10%, or about 40%, of the emitted fluorescence is received by single mode fiber 314.

Figure 4A:
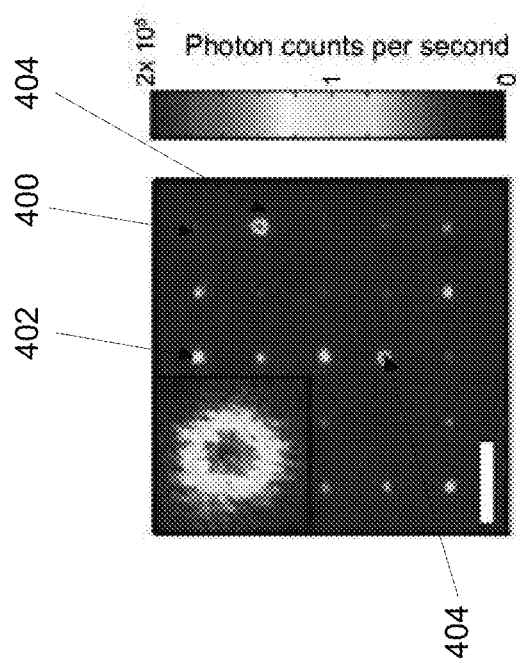
FIG. 4A is a confocal microscope image of a square array of diamond nanowires (scale bar 5 µm).
Figure 4B:
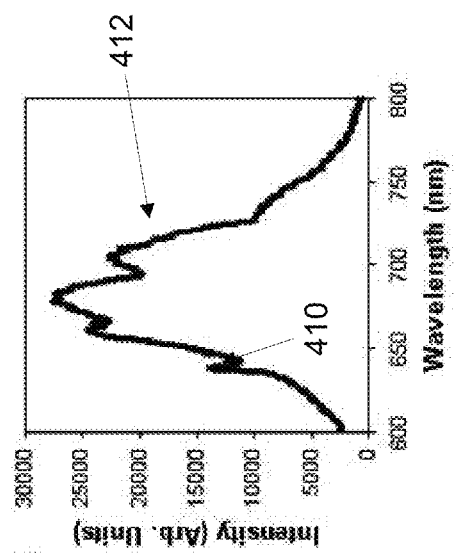
FIG. 4B is a photoluminescence spectrum of photons collected from a diamond nanowire containing an NV center.

Referring to FIGS. 4A and 4B, a confocal microscope image of a square nanowire array was obtained using optical system 300. A high-throughput screening technique was first used to scan large nanowire arrays in order to identify those nanowires exhibiting the highest count rates (i.e., those nanowires having embedded NV centers). The results of this screening step are shown in FIG. 4A. Light blue 400 and yellow 402 spots correspond to nanowires with no embedded NV center or to nanowires containing a weakly coupled NV center (e.g., off-axis NV centers, discussed in greater detail below), respectively. Diamond nanowires containing NV centers (i.e., diamond nanowires that act as efficient single photon sources) appear as red spots 404, indicating the high photon counts per second emitted from such nanowires. The properties of a single nanowire identified as containing an NV center were then studied for long periods of time (e.g., days) to demonstrate the structural stability of the nanowire and the photo stability of the embedded NV center. The results of this long-term study are shown in FIG. 4B. A photoluminescence spectrum of photons collected from a diamond nanowire including an NV center shows a zero-phonon line 410 corresponding to the NV center at about 637 nm and a phonon sideband 412 from about 640-780 nm.

The light emitted from diamond nanowires having embedded NV centers is non-classical in nature, rendering these nanowires useful for quantum device applications. To demonstrate the non-classical nature of the emitted light, single photons from an NV center coupled to a diamond nanowire were sent one-by-one through a 50-50 beam-splitter and were detected with an avalanche photodiode (APD) at each output channel (Hanbury Brown and Twiss configuration). The number of coincidence counts on each channel was measured as a function of time delay and normalized to the Poissonian source to give the corresponding second-order intensity auto-correlation function $g^{(2)}(\tau)$.

Referring to FIGS. 5A-5C, the presence of a single quantum emitter in the diamond nanowire is revealed by $g^{(2)}(\tau)$. Qualitatively different dynamics are observed at different excitation powers. Referring to FIG. 5A, at low pump powers (e.g., 11 µW, below saturation), strong photon anti-bunching ($g^{(2)}(0)<\frac{1}{2}$; i.e., a dramatic decrease at zero time delay) indicates that coupling between an NV center and its host nanowire dominates all other background sources, including stray light, APD dark counts, and substrate fluorescence. Referring to FIGS. 5B and 5C, at higher pump powers (e.g., 190 µW (at saturation) and 1.6 mW (above saturation), respectively), coupling to the metastable shelving state is significant. Bunching shoulders ($g^{(2)}(\tau)>1$) are observed at intermediate decay times due to optical cycling through a long-lived, non-radiative shelving state. In addition, the main features of the level crossing system that lead to the polarization mechanism of the $m_s=0$ sublevel of the triplet ground state and the spin-dependent fluorescence rate remain unchanged after nano-structuring. This result was also confirmed by standard electron spin resonance and Rabi measurements. Note that the curves in FIGS. 5A and 5B were fit using a three-level model of the $g^{(2)}(\tau)$ function.

Referring to FIG. 5D, the fluorescence lifetime of a color center (e.g., an NV center) in a diamond nanowire gives an upper bound on the number of single photons that may be collected. This is encoded in the temporal width of the autocorrelation data, whose exponential decay is of the form $\exp(-(r+\gamma)|\tau|)$ for low pump powers, where r is the pump rate, $\Gamma=1/\tau_{NW}$ is the NV center decay rate, and $\tau_{NW}$ is the NV center lifetime in the nanowire. That is, the fluorescence lifetime in the limit of zero pump power can be determined from the decay rate of the $g^{(2)}(\tau)$ function. The overall decay rate $1/\tau=r+\Gamma$ was measured at different pump powers and observed to decrease linearly at low pump powers, as shown in curve 500. The average lifetime of six different nanowire devices was observed to be $\tau_{NW}=14.6\pm1.9$ ns, which, as expected, is slightly longer than the lifetime of an NV center in bulk diamond (11.8 ns). The increased lifetime is consistent with the slight suppression of emission in nanowires. More generally, the average lifetime of a nanowire device is between about 10 ns and about 25 ns.

Referring to FIGS. 6A-6C, the dramatic benefits of nano-structuring are most directly observed by comparing the single photon flux from an individual NV center in a nanowire to an individual NV center in bulk diamond. The parameters of interest are $P_{sat}$, which is a measure of the level of optical power that saturates the NV center response; and $I_{sat}$, which is the number of single photon counts per second (cps) collected from the device. Experimentally, these parameters were extracted from a measurement of the device count rate for different pump powers. After a sharp rise at low pump powers (i.e., $P<P_{sat}$; features 600 and 602), the number of collected photons per second saturates at high powers ($I_{sat}$) due to the finite NV center emission rate, which is governed by the equation $I(P)=I_{sat}/(1+P_{sat}/P)$.

Referring now to FIG. 6A, a curve 604 represents the single photon L-L curve for a representative ultra-pure bulk diamond crystal NV device. This device was observed to have $I_{sat}=21\pm2$ kcps and $P_{sat}=990\pm540$ µW. Referring to FIG. 6B, a curve 606 represents the single photon L-L curve for a representative diamond nanowire NV device. The nanowire device was observed to have $I_{sat}=168\pm37$ kcps and $P_{sat}=58\pm37$ µW. This performance corresponds to about $2.5\times10^{-4}$ collected photons per NV center lifetime in the bulk device (FIG. 6A) and about $2.5\times10^{-3}$ in the nanowire antenna. More generally, the fluorescence emitted from a diamond nanowire NV device is at least 50 kcps, or at least 100 kcps. In both cases, laser power was measured in front of the microscope objective. Black points show raw count data from each device; hollow circles show linear background data measured off of the device; and gray circles show the net NV center counts. The NV center single photon L-L curves were fit using a saturation model, described in greater detail below.

Referring to FIG. 6C, single photon device parameters are shown in a plot of $I_{sat}$ versus $P_{sat}$, which demonstrates that a diamond nanowire single photon source exhibits in- and out-coupling of light that is an order of magnitude more efficient than a bulk diamond device. That is, nanowire-based devices are pumped an order of magnitude more efficiently (x-axis) than bulk devices and allow for an order of magnitude higher single photon flux (y-axis). Note that factors such as optical cycling through the metastable shelving state and losses in the optical system used in the experiment cause the observed single photon count levels to deviate from the theoretical maximum number predicted in simulations.

Simulation of Nanowire Emission

Three-dimensional finite-difference time-domain (FDTD) calculations predict that nanowire antenna devices (i.e., nanowires having embedded NV centers) improve the NV center single photon source. Coupling optical power from a pump laser to a nanowire waveguide with an embedded NV center allows for excitation that is an order of magnitude more efficient than in bulk diamond crystal. The nanowire also modifies the NV center far-field spectrum and facilitates collection of emitted photons with an objective lens.

Figures 7A, 7B:
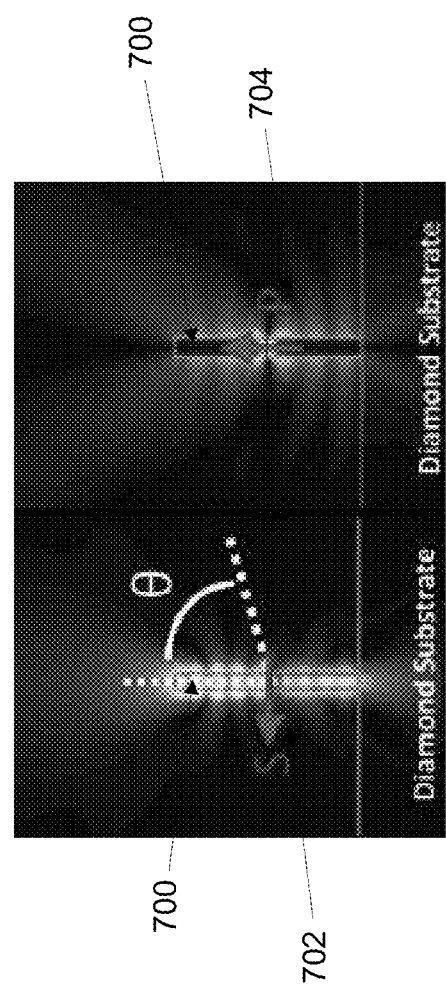
FIGS. 7A and 7B are finite-difference time-domain (FDTD) field profiles of a radial component of an electric field in a diamond nanowire having an s-polarized dipole and a p-polarized dipole, respectively.

Referring to FIG. 7A, the fundamental nanowire mode ($HE_{11}$) is the dominant emission (i.e., decay) channel for an s-polarized dipole (i.e., an NV center) positioned on the nanowire axis. More specifically, FIG. 7A shows a representative field profile of a radial component of the electric field ($E_r$) for a 2 µm long, 200 nm diameter diamond nanowire 700 with an on-axis s-polarized dipole 702 emitting at λ=637 nm (the zero-phonon line wavelength of the NV center) positioned at the nanowire center. Highly directional emission from the nanowire's top facet, contained within the collection angle (NA~0.95; θ~72°) of an objective lens positioned above the nanowire, allows for roughly 100% of the vertically emitted photons to be collected.

Referring to FIG. 7B, a p-polarized dipole (i.e., an NV center) does not emit into the waveguide mode due to symmetry mismatch, but can still emit into vertically propagating radiation modes. Specifically, FIG. 7B shows a representative $E_r$ field profile for the nanowire 700 of FIG. 7A, with a p-polarized dipole 704 positioned on the nanowire axis. Emission into upward propagating radiation modes still allows for significant collection by an objective lens.

For an NV center dipole polarized in the {111} plane of a {100} diamond nanowire, which contains both s- and p-components, about 40% of emitted photons are collected from a nanowire, as compared to about 3% from a bulk diamond crystal. A fluorescence lifetime that is intermediate between bulk diamond, where the NV center lifetime is short (~12 ns) due to the large background refractive index (n~2.4), and an NV center in a diamond nanoparticle (~25 ns) which resembles a dipole in air (n~1) is expected. Overall, the diamond nanowire increases the photon flux from an individual NV center by an order of magnitude as compared to a bulk diamond crystal.

More generally, FDTD simulations were performed assuming a nanowire having a circular cross section and a diameter d. Two general polarization scenarios were considered for a dipole (NV center)/nanowire system: dipolar polarization perpendicular (s-polarized) and parallel (p-polarized) to the nanowire axis. The dipole associated with an NV center in {100} diamond can be represented using a combination of these two dipoles, because such a dipole is polarized in the {111} plane. At different wavelengths within the NV center's radiation spectrum (637 nm-780 nm), the number of collected photons can be expressed as $\Gamma(\lambda)\cdot\eta(\lambda)$, where $\Gamma$ is the emission rate (reciprocal to the lifetime) and η is the collection efficiency.

Figure 8:
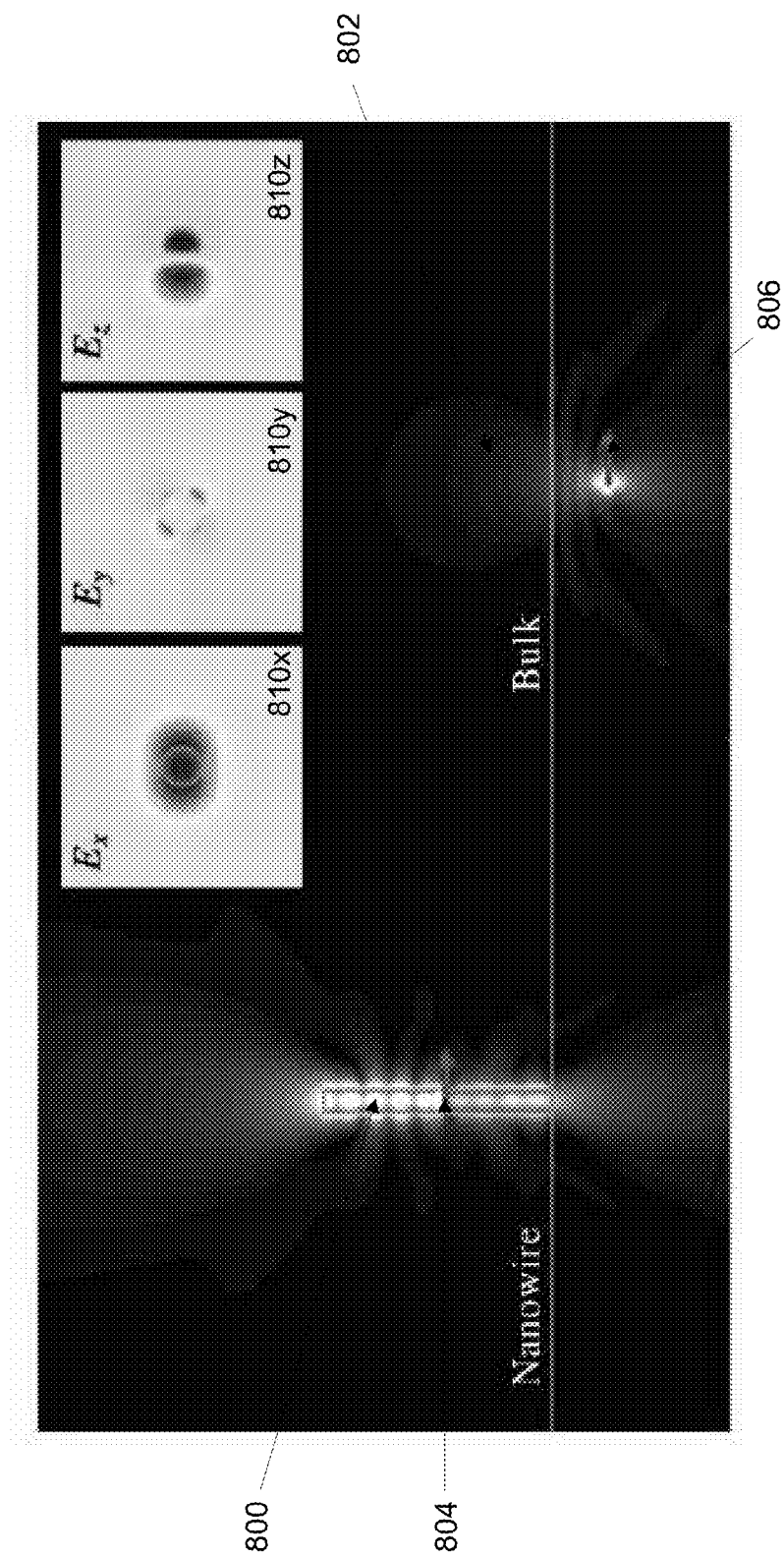
FIG. 8 is a plot of a field profile of the radial component of an electric field for a nanowire (left) and a bulk diamond (right). Insets depict the electric field associated with the fundamental nanowire waveguide mode ($HE_{11}$).

Referring to FIG. 8, a field profile shows the radial component of the electric field ($E_r$) for a 2 µm long, 200 nm diameter diamond nanowire (left; feature 800) and a bulk diamond (right; feature 802). The collection efficiency can be dramatically improved in diamond nanowires as compared with bulk diamond. The dipole in each case (804 and 806, respectively) is polarized parallel to the interface and emits at λ=637 nm (the zero-phonon line wavelength of the NV center).

The field profiles in FIG. 8 show that the major portion of light emitted from an NV center in bulk diamond leaks to the substrate due to significant total internal reflection at the diamond-air interface, whereas in a diamond nanowire the fundamental $HE_{11}$ mode is the dominant emission channel for a dipole polarized perpendicular to the nanowire axis (in the xy plane). X-, y-, and z-components (810x, 810y, 810z, respectively) of the $HE_{11}$ mode are shown in the insets of FIG. 8. This waveguide mode directs the light propagating in the nanowire, and is scattered vertically as it exits from the top nanowire facet. This process allows for efficient collection using an objective lens positioned above the nanowire.

Figure 9:
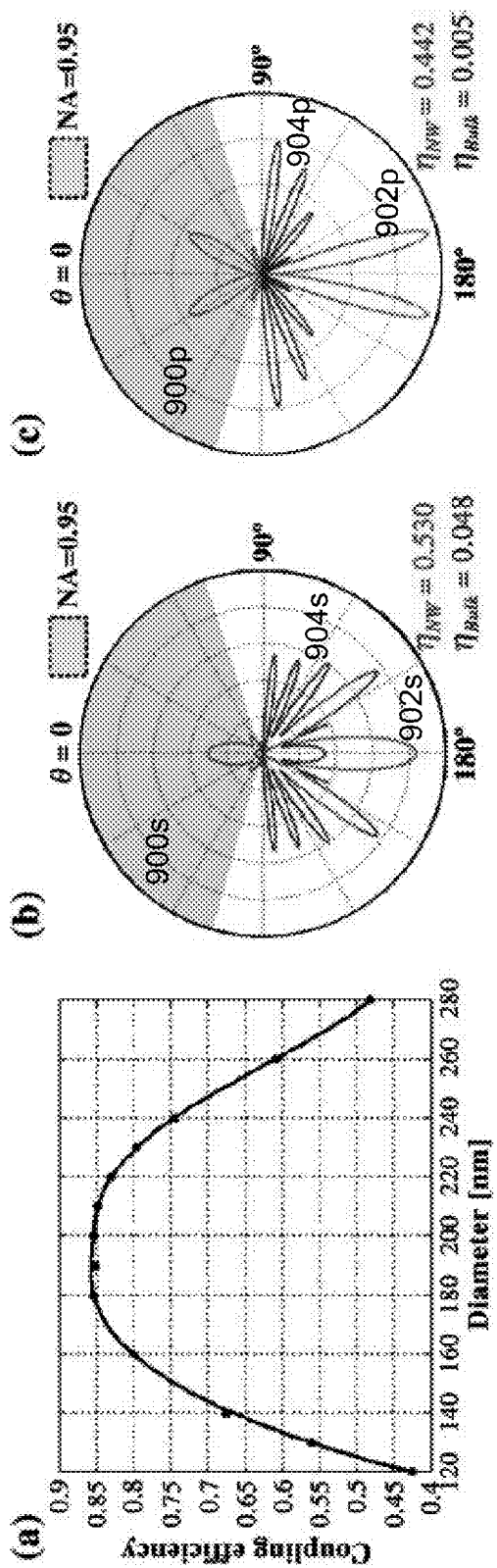
FIG. 9A is a plot of coupling efficiency as a function of nanowire diameter for λ=637 nm.
FIGS. 9B and 9C show the far-field profiles of power emitted from an s-polarized and a p-polarized dipole, respectively, embedded at the center of a nanowire and in a bulk diamond crystal.

Referring to FIG. 9A, the coupling efficiency, α, between the NV center and the nanowire waveguide mode is shown as a function of the nanowire diameter, for wavelength λ=637 nm. In the case of an s-polarized dipole placed at the center of the nanowire, more than 80% of the emitted photons couple to the nanowire mode for a broad range of nanowire diameters (180 nm-230 nm). In the examples discussed herein, 200 nm diameter nanowires were used in order to optimize the coupling efficiency.

Referring to FIGS. 9B and 9C, photon collection efficiencies can be quantified form the far-field profile of power emitted upward. An objective lens with a numerical aperture NA=0.95, positioned above the nanowire, can collect light emitted into the solid angle of 72° (represented by shaded areas 900s and 900p for s- and p-polarized dipoles, respectively, in the far-field emission profiles). In the case of both s- and p-polarized dipoles, almost 100% of the photons emitted form the nanowire can be collected with the lens. This is true even for p-polarized dipoles, despite the fact that a symmetry mismatch prevents coupling to the nanowire waveguide mode. In the case of p-polarized dipoles, however, large collection efficiency is enabled by coupling to radiative modes that are also modified by the presence of the nanowire. Furthermore, comparing a dipole in a nanowire (lines 902s and 902p) with a dipole in a bulk diamond crystal (lines 904s and 904p) shows that the nanowire geometry provides an improvement of one and two orders of magnitude in the collection efficiency for s- and p-polarized dipoles, respectively.

The total emission rate (the reciprocal of lifetime) of an NV center in a nanowire is dependent on the position of the NV center. Fabry-Perot resonances, formed due to the (weak) reflection of a waveguide mode by the facets of a nanowire, can modify the emission rate of an s-polarized dipole. This is reflected in the enhancement factor (also known as the Purcell factor) $E(\lambda)=\Gamma(\lambda)/\Gamma_0(\lambda)$, where $\Gamma_0$ is the emission rate of the quantum emitter in a homogeneous diamond medium. The enhancement factor describes the modification of the NV center fluorescence lifetime in a nanowire ($\tau_{NW}=1/\Gamma_{NW}$) compared to the bulk ($\tau_{bulk}=1/\Gamma_{bulk}$) For λ=637 nm and for a nanowire of 200 nm diameter, the enhancement factor is in the range of 0.65-1.10, depending on the dipole position along the axis of the nanowire. The collection efficiency for an s-polarized dipole is maximized (shown in FIG. 9B) when destructive interference occurs between downward emitted photons and photons reflected from the top nanowire facet (see, e.g., FIG. 8). This case favors upward emission at the expense of slightly increased radiative lifetime.

The theoretically accessible single photon flux is described by the following figure of merit:

$$N = \frac{\int\int E(\lambda, \sigma)\eta(\lambda, \sigma)I(\lambda)d\sigma d\lambda}{2\pi\int I(\lambda)d\lambda},$$

where λ is the dipole wavelength and σ is the dipole polarization. That is, the total number of collected photons is obtained by averaging over wavelengths and polarizations, taking into account both s- and p-polarized components of the NV dipole as well as its broadband emission due to the phonon sideband. The enhancement factor E(λ) was evaluated by comparing total emitted power from a dipole in a diamond nanowire to the emitted power in a homogeneous diamond medium (n=2.4). The collection efficiency η was calculated from the overlap of the dipole far-field pattern with the acceptance angle of the microscope objective (NA~0.95). Parameters $F_P$ and η are wavelength and polarization dependent and were integrated against the room temperature NV fluorescence spectrum I and over the (111) dipole plane of a (100) diamond crystal. These parameters were calculated for both nanowire ($N_{NW}$~0.3) and bulk ($N_{bulk}$~0.033) single photon sources; the ratio of these values gives the expected order of magnitude improvement in single photon flux due to nanostructuring.

Fabrication of Diamond Nanowire Arrays

Top-down nanofabrication techniques were used to define large (e.g., as large as hundreds of square microns; see FIG. 1B) arrays of vertically oriented nanowire antennas in a single crystal diamond substrate. Top-down fabrication maintains the optical properties of the NV centers and is compatible with requirements for the realization of scalable diamond-based quantum systems. Because NV centers are distributed randomly throughout the substrate, the formation of nanowires isolates individual NV centers and minimizes background fluorescence.

Figure 10:
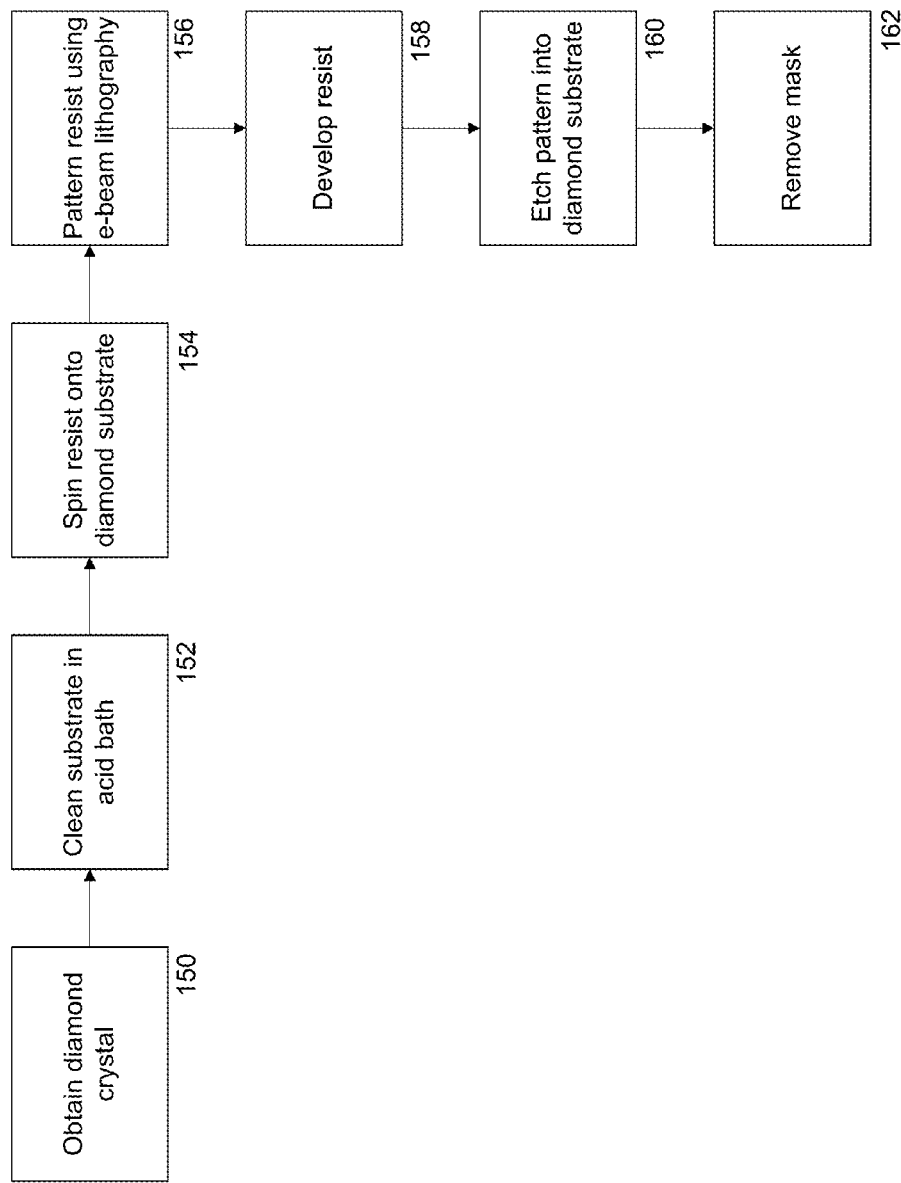
FIG. 10 is a flow chart showing the steps in fabricating a diamond nanowire array.

Referring to FIG. 10, a nanowire array was prepared from a commercially available (Element 6 Corporation, New York, N.Y.) high-pressure, high-temperature, ultra-pure Type Ib (nitrogen rich) or IIa (nitrogen content<0.1 ppm) diamond crystal synthesized via HPHT and chemical vapor deposition (CVD) processes, respectively, and including randomly embedded NV centers (step 150). The surface of the diamond substrate is generally a {100} or {111} type surface. The single crystal bulk diamond substrate was cleaned in a boiling 1:1:1 Nitric, Perchloric, and Sulfuric acid bath for about 45 minutes to remove surface contamination (step 152).

A 1:2 dilution of FOx 17 negative electron beam (e-beam) resist (Dow Corning, Midland, Mich.) with methyl isobutyl ketone (MIBK) was spun onto the cleaned substrate to form a resist layer (step 154). Arrays of ~200 nm diameter circles were patterned in the resist using an Elionix (Billerica, Mass.) e-beam writing system at a dosage of about 6000 μC/cm² (step 156). 25% Tetra-methyl ammonium hydroxide (TMAH) was used to develop the resist and form the etch mask (step 158).

The diamond crystal with patterned resist was then placed in an inductively coupled plasma (ICP) reactive ion etch (RIE) system and etched for 10 minutes with 30 sccm of Oxygen gas, 100 W bias power, and a 10 mTorr chamber pressure (step 160). For the first two minutes, 700 W of ICP power was applied, followed by three minutes of 600 W ICP power, and finally five minutes of 1000 W ICP power. An HF wet etch was used to remove the mask from the top of the nanowires (step 162); an additional acid bath treatment was performed prior to device testing. The resulting nanowires were about 200 nm in diameter and 2 μm long, with straight, smooth sidewalls.

Other etch masks can also be used to define the nanowires. In one embodiment, nanoparticles deposited via drop-casting are used as an etch mask. In an alternative embodiment, a gold mask defined via a lift-off process is used as an etch mask. In another embodiment, a spin-on-glass mask is defined by electron beam lithography.

Although single crystalline diamond is generally preferable to realize single photon sources, in other embodiments, polycrystalline diamond (poly-D) films (e.g., 2 μm polycrystalline diamond on 1 μm thermal $SiO_2$ on a silicon substrate; Advanced Diamond Technologies, Inc.) were used due to their low cost and availability in large quantities. Prior to mask deposition and reactive ion etching, all poly-D samples were solvent cleaned but were not acid bath cleaned to avoid damage.

Implantation of Nitrogen Vacancy Centers

The above-described fabrication process relies on the random natural distribution of NV centers in bulk diamond crystal. In an alternative embodiment, NV centers are implanted into diamond using ion implantation.

In a first embodiment, Nitrogen is implanted into a bulk diamond crystal via a low-energy, "shallow" (~20 nm deep) ion implantation process. Individual NV centers are then isolated mechanically by dry etching, generating large and regular arrays of diamond nanopillars. This deterministic fabrication technique could be used to facilitate the coupling of single NV centers to proximal nanophotonic devices.

Figure 11:
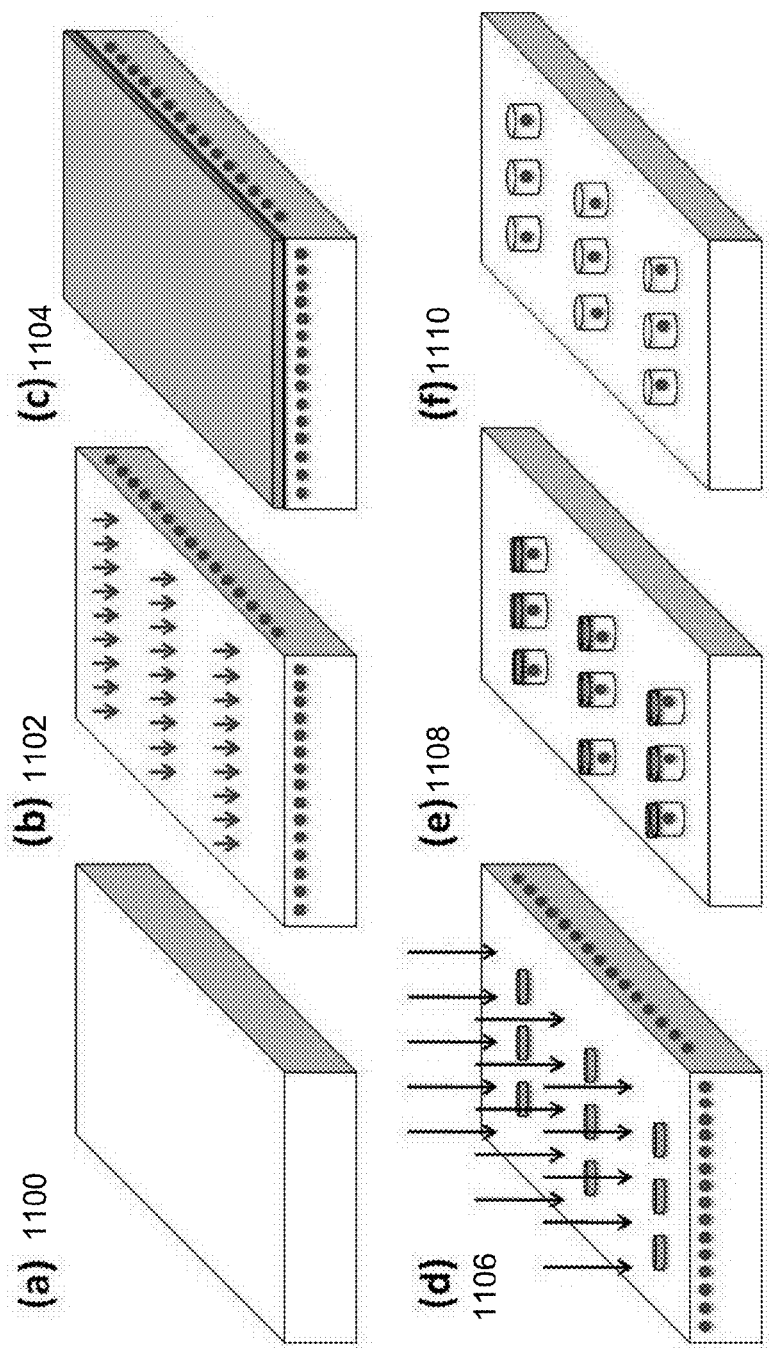
FIG. 11 is a block diagram showing ion implantation for the generation of diamond nanopillars containing embedded NV centers.
Figure 12:
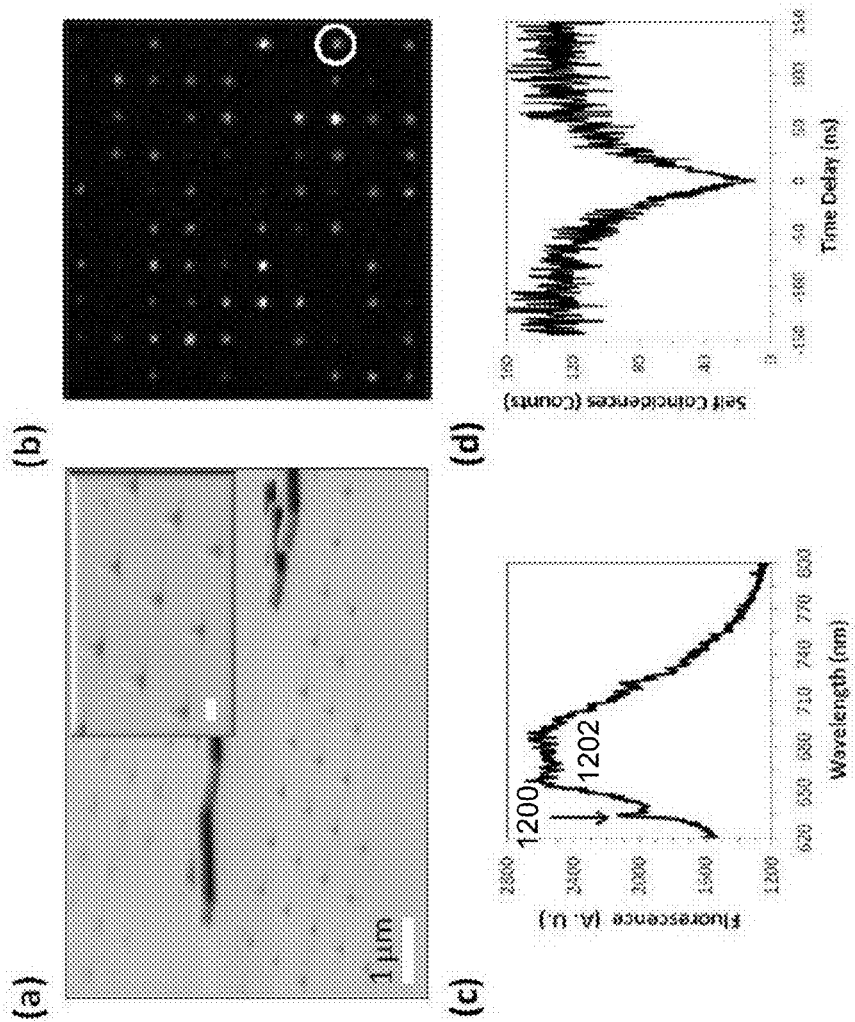
FIGS. 12A and 12B are SEM and confocal microscopy images, respectively, of a nanopillar array generated according to the process shown in FIG. 11.
FIGS. 12C and 12D are a photoluminescence spectrum and a plot of the fluorescence intensity autocorrelation function, respectively, collected from one of the nanopillars of FIG. 12A.

Referring to FIG. 11, high quality electronic grade type IIa CVD diamond (Element 6) with low (<5 ppb) background Nitrogen content (step 1100) was implanted with $^{15}N$ ions at an energy of 14 keV and a dosage of $1.25*10^{12}$ cm$^{-2}$. Stopping Range of Ions in Matter (SRIM) calculations project a Nitrogen layer about 20 nm below the surface. The Nitrogen-implanted sample was annealed at 750° C. for 2 hours in high vacuum (<$10^{-6}$ Torr) in order to mobilize vacancies, generating a shallow layer of NV centers (step 1102). Electron beam lithography resist is deposited on the diamond surface (step 1104) and arrays of circular shapes with ~65 nm radius were defined on the top surface using electron beam lithography (Elionix; step 1106). Reactive ion etching in oxygen was applied for one minute, generating pillars about 200 nm tall on the top of the diamond surface (step 1108). The sample was then placed in a hydrofluorice acid wet etch for approximately 20 seconds to remove the residual mask layer and then in a 1:1:1 mixture of Sulfuric, Nitric, and Perchloric acid at 400° C. for about 30 minutes to clean the sample (step 1110).

Referring to FIGS. 12A-12D, an SEM image of an array of nanopillars fabricated in this way (FIG. 12A) reveals nanopillars with a height of ~250 nm and a radius of ~65 nm. The diamond sample including nanopillars was characterized using confocal microscopy. The fluorescence (FIG. 12B) emitted under 532 nm continuous wave (CW) excitation shows a regular array of bright white spots corresponding to the nanopillars in the SEM image of FIG. 12A. The photoluminescence spectrum (FIG. 12C) of the nanopillars shows a characteristic zero-phonon line 1200, at ~634 nm, as wells as a broad phonon sideband 1202 of an embedded NV center. Based on measurements of the fluorescence intensity autocorrelation function (FIG. 12D), strong photon anti-bunching was observed, indicating that one, two, or three NV centers are embedded in any given nanopillar. In general, a high yield (at least 10%) of the nanopillars fabricated in this manner contain a single NV center and thus operate in the single photon regime.

Figure 13:
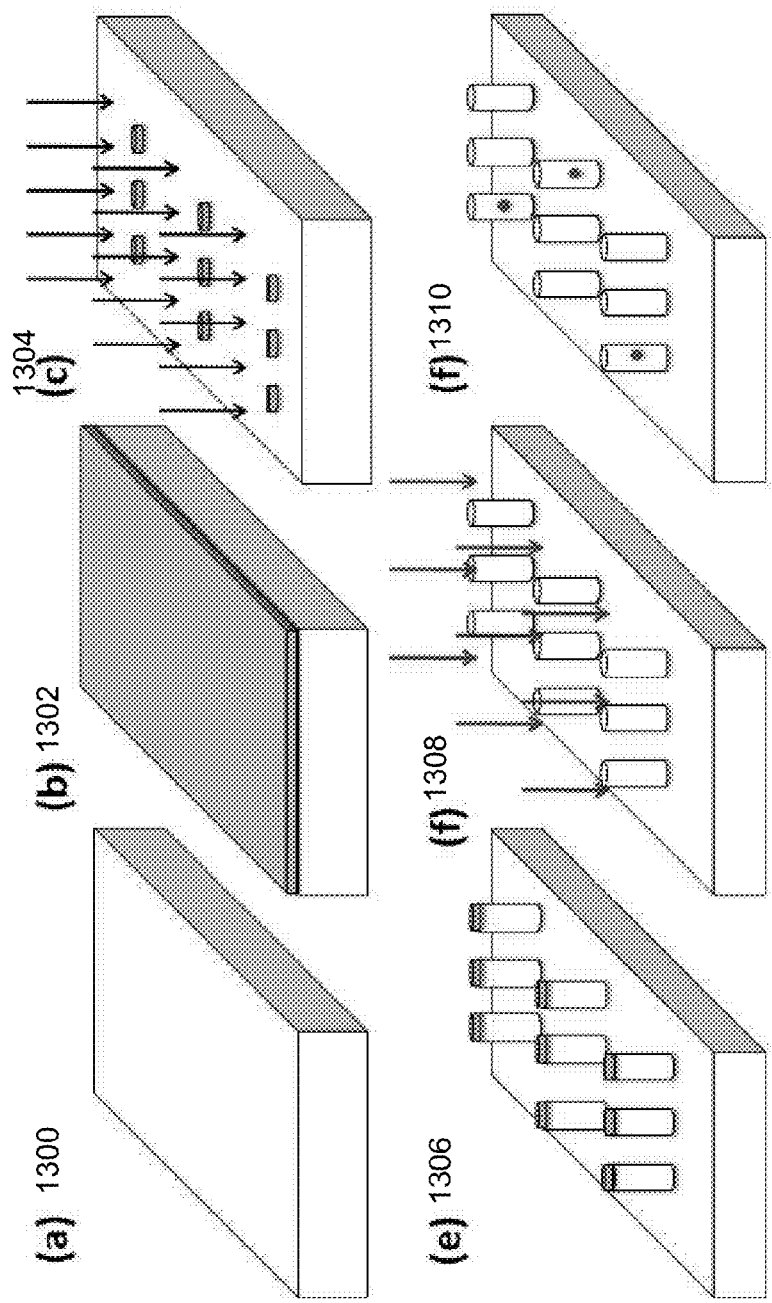
FIG. 13 is a block diagram showing ion implantation to generate NV centers in an array of diamond nanowires.

Referring to FIG. 13, in a second embodiment, Nitrogen is implanted at low density into prefabricated diamond nanowire via a high-energy, "deep" (~1 μm) ion implantation process. An array of nanowires (~200 nm diameter, ~2 μm height) were fabricated, e.g., using the top-down fabrication techniques described above (steps 1300-1306). The fabricated devices were then implanted with $^{15}$N at 1.7 MeV and $1*10^9$ cm$^{-2}$ dosage (step 1308) and annealed at 750° C. in high vacuum (<10$^{-6}$ Torr) for 2 hours (step 1310). SRIM calculations indicate that this produces a layer of NV centers ~1.0 μm below the diamond surface.

The yield of nanowires containing an NV center is relatively low due to the reduced implantation dosage. In order to identify a successfully implanted device, a 532 nm CW laser was scanned over large sections of the nanowire array at high powers (~3 mW) in order to bleach the background fluorescence from the nanowire devices. Implanted nanowires demonstrated sustained brightness due to the photo-stability of the NV center.

Figure 14:
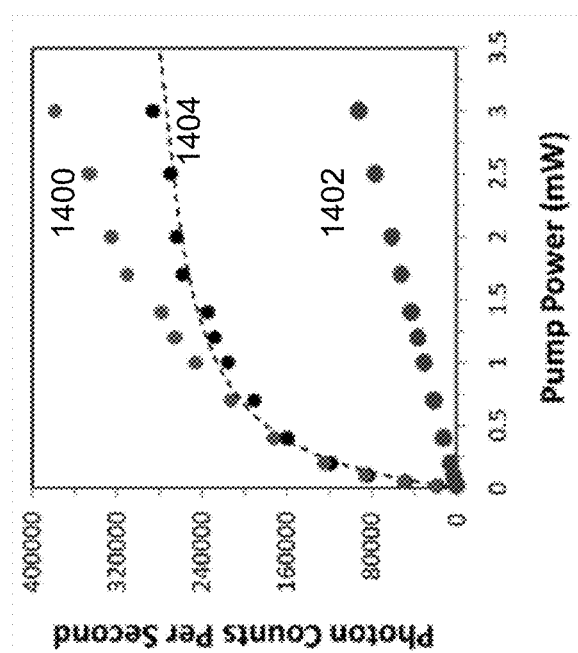
FIG. 14 is a plot of the photon counts per second as a function of pump power for an implanted NV center in a diamond nanowire.

Referring to FIG. 14, the light in-light out curve demonstrates that an implanted nanowire may act as a high-flux single photon source. A curve 1400 depicts the total nanowire fluorescence from a single device; a curve 1402 shows the background fluorescence obtained from contrast in photon anti-bunching data; and a curve 1404 shows the remainder of the net single photon counts from an embedded NV center. The number of single photons collected from the nanowire was observed to turn on sharply at low pump powers and saturate at high powers. The saturation counts per second $CPS_{sat}$=304,000 and the saturation pump power $P_{sat}$=0.34 mW are consistent with efficient excitation and extraction of single photons from an NV center.

Other Embodiments

In addition to NV centers, other color centers may be used, such as color centers based on Silicon, Carbon, Nickel, or Chromium.

Although the measurements described above were performed at room temperature, the nanowire-embedded NV center can also function at low temperatures (e.g., cryogenic temperatures, about 4 K). High single photon flux and other functionality of the device still apply at low temperatures. Low temperature operation is relevant to certain communications applications.

Diamond nanowires including color centers may be integrated into more complex photonic and quantum information processing devices and quantum cryptography devices. In these devices, more advanced functions such as increasing photon production rate via the Purcell effect will enable devices operating at even higher count levels and lower powers. For instance, a diamond nanowire with a single color center may act as an antenna and may be interfaced with an optical fiber for communication purposes. By implanting color centers in diamond nanowires, simultaneous optimization of both spin and optical properties is possible in a single device.

In a diamond nanowire photonic array, a number of channels may be addressed simultaneously.

Diamond nanowires are biologically compatible and can be used in biological applications. For instance, a plurality of diamond nanowires disposed on a substrate can be used to deliver chemicals to biological systems by coating the diamond nanowires with the desired chemical and puncturing target cells with the coated diamond nanowires. Furthermore, the light emitting capabilities of the diamond nanowires may be relevant for integration in biological systems.

The high precision fabrication methods described herein allow diamond nanowires to be used in microelectromechanical (MEMS) and nanoelectromechanical systems (NEMS), sensing, and scanning probe microscopy. For instance, a single diamond nanowire may be used as a mechanical resonator or an atomic force microscopy (AFM) cantilever.

Embedding nanopillar arrays in a metal layer could allow for plasmon-enhanced single photon emission. Furthermore, nanopillar or nanowire arrays could offer convenient, evanescent coupling to other proposed photonic crystal cavities in semiconductor material systems for cavity quantum electrodynamics studies. In general, the scalability of the nanowire system is an attractive resource for the development of more complex and integrated device architectures.

There are several natural extensions of the deep implantation of color centers into nanowires. The combination of high directionality of emission from the nanowire antenna combined with low background fluorescence in the pure diamond crystal allows for a significant reduction in the requirements on optical systems used to probe a single color center. For instance, it is possible to observe anti-bunching as strong as $g^{(2)}(0)$~0.1 in a confocal microscope with a lower numerical aperture of NA~0.6, though at slightly reduced collection efficiency. Classical lightwave technology can also be integrated with a quantum optical light source by coupling the emission of a single NV center directed to a lensed optical fiber (NA~0.4) via a diamond nanowire antenna.

In general, the nanowire architecture provides a general setting for conducting studies of the low-temperature properties of an NV center (e.g., stability of optical transitions, effects of strain) in diamond nanophotonic structures.

It is to be understood that the foregoing description is intended to illustrate and not to limit the scope of the invention, which is defined by the scope of the appended claims. Other embodiments are within the scope of the following claims.

What is claimed is:

1. A system comprising:
    a plurality of diamond nanowires disposed on the surface of a diamond substrate that includes a plurality of color centers, at least some of the nanowires formed in the substrate with portions of the surface of the substrate selectively removed in a region including at least one color center to include a color center in at least some of the nanowires;
    a light source configured to illuminate at least one of the plurality of nanowires with excitation light at a wavelength corresponding to an excitation wavelength of the color center included in the illuminated nanowire; and
    an optical receiver configured to receive a fluorescence emitted from the color center included in the illuminated nanowire in response to the excitation light.

2. The system of claim 1, wherein the optical receiver is at least one of an optical fiber and a detector.

3. The system of claim 1, wherein each nanowire has a diameter of about 200 nm and a length of about 2 μm.

4. The system of claim 3, wherein the length of the nanowires is in a direction perpendicular to the surface of the substrate.

5. The system of claim 1, wherein a lifetime of the fluorescence emitted from the at least one color center is between about 10 ns and about 25 ns.

6. The system of claim 1, wherein a first end of the illuminated nanowire is in contact with the surface of the substrate, and wherein the optical receiver is positioned to receive the emitted fluorescence from a distal end of the illuminated nanowire.

7. The system of claim 1, wherein the fluorescence is emitted from the at least one color center in a mode propagating substantially perpendicularly away from the surface of the substrate.

8. The system of claim 1, wherein the optical receiver is positioned to receive at least 10% of the emitted fluorescence.

9. The system of claim 1, wherein the fluorescence includes at least 100,000 photons per second.

10. The system of claim 1, wherein the illuminated nanowire is configured to emit fluorescence at a temperature greater than about 300 K.

11. A method comprising:
providing a diamond substrate that includes a plurality of color centers; and
selectively removing a portion of the surface of the substrate to provide a plurality of diamond nanowires, including selectively removing a portion of the surface of the substrate in a region including at least one color center.

12. The method of claim 11, wherein the plurality of color centers in the diamond substrate are distributed substantially randomly.

13. The method of claim 11, further comprising implanting at least one color center in at least some of the plurality of diamond nanowires.

14. The method of claim 11, further comprising forming a microelectromechanical systems (MEMS) or nanoelectromechanical systems (NEMS) device including at least one of the plurality of diamond nanowires.

15. The method of claim 14, wherein the MEMS or NEMS device includes at least one of a mechanical resonator and an atomic force microscopy (AFM) probe.

16. The method of claim 11, further comprising:
illuminating at least some of the plurality of nanowires with excitation light at a wavelength corresponding to an excitation wavelength of the nitrogen vacancy centers; and
receiving a fluorescence emitted from at least one nitrogen vacancy center in response to the excitation.

17. The method of claim 16 wherein receiving the fluorescence includes detecting at least 10% of the emitted fluorescence.

18. The method of claim 16, wherein receiving the fluorescence includes receiving the fluorescence into an optical fiber.

19. The method of claim 11, wherein selectively removing a portion of the surface of the substrate includes fabricating nanowires with diameter of about 200 nm and a length of about 2 μm.

20. The method of claim 11, wherein selectively removing a portion of the surface of the substrate includes:
lithographically defining a pattern on the surface of the substrate corresponding to an arrangement of the nanowires; and
etching the surface of the substrate according to the lithographically defined pattern.

21. The method of claim 20, wherein etching the surface of the substrate includes performing a reactive ion etch for about 10 minutes.

22. The method of claim 21, wherein performing the reactive ion etch includes: applying an inductively coupled plasma (ICP) power of about 700 W for about two minutes; applying an ICP power of about 600 W for about three minutes; and applying an ICP power of about 1000 W for about five minutes.

23. The method of claim 21, wherein performing the reactive ion etch includes performing the etch under at least one of the following conditions: in an atmosphere of 30 sccm of oxygen gas, at a pressure of 10 mTorr, and at a bias power of about 100 W.

* * * * *